(12) United States Patent
Vollbrecht

(10) Patent No.: US 7,815,585 B2
(45) Date of Patent: Oct. 19, 2010

(54) ADJUSTABLE ORTHOSIS

(75) Inventor: Matthias Vollbrecht, Herzberg (DE)

(73) Assignee: Otto Bock HealthCare IP GmbH & Co. KG, Duderstadt (DE)

( * ) Notice: Subject to any disclaimer, the term of this patent is extended or adjusted under 35 U.S.C. 154(b) by 0 days.

(21) Appl. No.: 11/994,884

(22) PCT Filed: May 9, 2006

(86) PCT No.: PCT/DE2006/000812

§ 371 (c)(1),
(2), (4) Date: Jan. 7, 2008

(87) PCT Pub. No.: WO2007/003148

PCT Pub. Date: Jan. 11, 2007

(65) Prior Publication Data

US 2008/0208090 A1  Aug. 28, 2008

(30) Foreign Application Priority Data

Jul. 5, 2005 (DE) .................. 10 2005 031 867

(51) Int. Cl.
*A61F 50/00* (2006.01)
(52) U.S. Cl. .................. 602/19; 602/5; 602/12
(58) Field of Classification Search .......... 602/2, 602/12, 19, 60–64, 75; 128/96.1, 100.1, 128/101.1; 2/311, 312

See application file for complete search history.

(56) References Cited

U.S. PATENT DOCUMENTS

| | | | |
|---|---|---|---|
| 1,893,960 A | 12/1931 | Pease | |
| 4,556,055 A | 12/1985 | Bonner, Jr. | |
| 5,363,863 A | 11/1994 | Lelli et al. | |
| 5,823,984 A | 10/1998 | Silverberg | |
| 2005/0228325 A1 | 10/2005 | Zours et al. | |
| 2006/0129077 A1* | 6/2006 | Parizot | ......... 602/19 |

FOREIGN PATENT DOCUMENTS

| | | |
|---|---|---|
| DE | 6943014 | 10/1969 |
| DE | 2837620 | 1/1981 |
| DE | 29803417 | 7/1998 |
| DE | 20204747 U1 | 8/2002 |
| GB | 2093699 * | 9/1982 |
| WO | 0137764 | 5/2001 |
| WO | 2004/065677 | 8/2004 |

OTHER PUBLICATIONS

International Search Report on PCT/DE2006/0008, 4 pages.

* cited by examiner

*Primary Examiner*—Kim M Lewis
(74) *Attorney, Agent, or Firm*—Faegre & Benson LLP

(57) ABSTRACT

A lower back orthosis bandage includes a middle piece having a first flat end and a second flat end, a first end piece having a mouth-like end and a second end piece having a mouth-like end. The first end piece is releasably connected to the first flat end of the middle piece by the mouth-like end of the first end piece. The second end piece is releasably connected to the second flat end of the middle piece by the mouth-like end of the second end piece. The first end piece and the second end piece are connectable to each other to close the bandage.

13 Claims, 3 Drawing Sheets

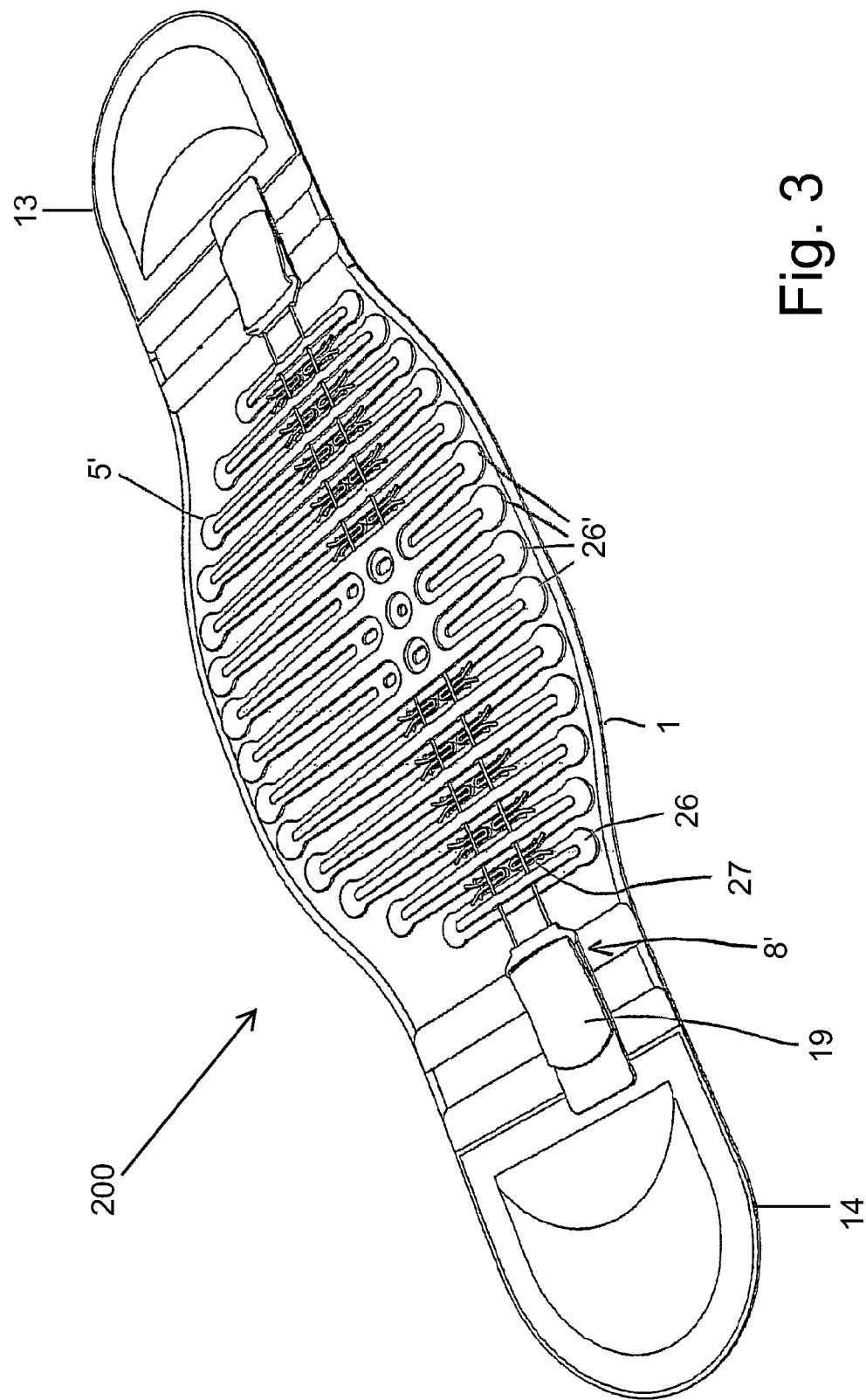

ADJUSTABLE ORTHOSIS

CROSS-REFERENCE TO RELATED APPLICATIONS

This patent application is the national stage application of International Application No. PCT/DE2006/000812, which claims priority to German Application No. 10 2005 031 867.3 filed Jul. 5, 2005; the entire contents of both applications are hereby expressly incorporated by reference.

BACKGROUND

The invention relates to a lower back orthosis including a bandage designed to surround the lower back of a patient.

Orthoses of the type referred to herein are used to encircle a body part of a patient, in particular the lower back of the patient. Such an orthosis may include supporting elements so that it may be used, for example, as a lower back orthosis to support and relieve the lumbar spine. It is known that the orthosis may need to perform different functions depending on the size of the patient and the condition to be treated.

For instance, it may be necessary to relieve the lordosis area of the spine in its entirety by bridging the area with a support device that provides for a substantial immobilization of the spine. It is also known that the lumbar area or lumbosacral area of the spine may be supported during limited mobility. In an advanced rehabilitation phase it may only be necessary to provide a certain degree of support by means of a bandage or a slightly reinforced bandage.

DE 202 04 747 U1 discloses a lower back orthosis, which is designed for use in different applications and for adjustment to different patients. The orthosis includes two overlapping constituent bandages, which allow the bandage height to be adapted to the patient in question, as well as various support devices attachable to the bandage. In addition to support rods that can be inserted into specially provided pockets, various support devices in the form of a back-support frame to bridge the lordosis area (lordosis correction) or a vertebral link pad to stabilize the movable lordosis area can also be secured to the bandage arrangement. If necessary, this spinal column orthosis can be supplemented with a dish-shaped abdominal pad. The various support devices can be attached to the bandage by means of a fastening connection, such as for example, Velcro® fasteners, and can thus be easily changed.

Known orthoses are made having different lengths in order to accommodate differences in the girth of the body part around which the bandage is wrapped. A finely differentiated range of lengths is not provided because the ends of the orthosis can overlap to a greater or lesser extent. However, a substantial overlap may occur in cases where the girth of the body part in question is small, adversely affecting the fit of the orthosis. Similarly, certain types of orthoses may not fit arounds patients with significant girths.

SUMMARY

One embodiment of the present invention is a lower back orthosis including a middle piece having first and second ends and first and second end pieces releasably securable to the respective first and second ends of the middle piece. The first end piece and the second end piece are also releasably securable to each other to close the orthosis around a patient. The lower back orthosis also includes first and second intermediate pieces, which are releasably securable between the respective first and second ends of the middle piece and the first and second end pieces to optionally increase its length. In one embodiment, the middle piece has a widened portion that has a greater width than the width of the end pieces for supporting the lower back. In another embodiment, the middle piece has a greater length than the end pieces and/or intermediate pieces.

In another embodiment, the first and second ends of the middle piece may include flat end portions, and the first and second end pieces may have mouth-like ends. The mouth-like ends of the end pieces are releasably securable over the flat ends of the middle piece. Each intermediate piece may also include a flat end and a mouth-like end such that is can be optionally releasably secured between the middle and end pieces. Releasable securement may be accomplished by attachment elements provided on one piece of the orthosis that may be secured to counter attachment elements provided on an adjacent piece.

Another embodiment is a method of positioning a lower back orthosis on a patient. The girth of the patient is determined and then compared to the length of the lower back orthosis. If needed, first and second intermediate pieces are releasably attached between a middle piece and opposing first and second end pieces of the lower back orthosis. The middle piece supports the patient's lower back. The end pieces are releasably secured at the patient's abdomen.

In additional embodiments, the connection between the parts is formed by means of fasteners which extend across the entire width of the bandage so that there is a large closure-contact area. In this way it is possible to produce a connection so that the orthosis encircles a body part, e.g. the lower back, under a certain tension. The orthosis can be formed having several lengths. A first, shortest length is formed by attaching the end pieces directly to the middle piece. Longer lengths are formed by inserting, between the middle piece and each of the two end pieces, intermediate pieces of the same length as each other. The intermediate pieces may be longer or shorter than the middle piece, the end pieces or each other.

It is also possible to connect several intermediate pieces together to produce longer lengths. It may be, however, preferable to use intermediate pieces of different lengths so that the number of connections does not become too great.

The strength of the connection between the parts of the orthosis may be increased by one part of the orthosis having a flat end with fastener elements attached on both sides of the flat end and by another part that is to be connected to the flat end having a mouth-like end which goes over both sides of the flat end and which has fastener counter-elements on the inner surfaces that lie against the flat end. This doubles the effective closure-contact area of the fastener elements between the parts without it being necessary to increase the size of the fastener strips lengthways along the bandage. Furthermore, this design counteracts the development of torque in the direction of unfastening the fasteners as the resistance to traction operates on both sides of the connected-together ends of the parts of the orthosis.

The invention will be explained in greater detail below with the aid of an embodiment example shown in the drawings.

BRIEF DESCRIPTION OF THE DRAWINGS

FIG. 3 shows a perspective view as in FIG. 2 with an attached supporting element with a tightening belt through the supporting element.

DETAILED DESCRIPTION

Figure 1:
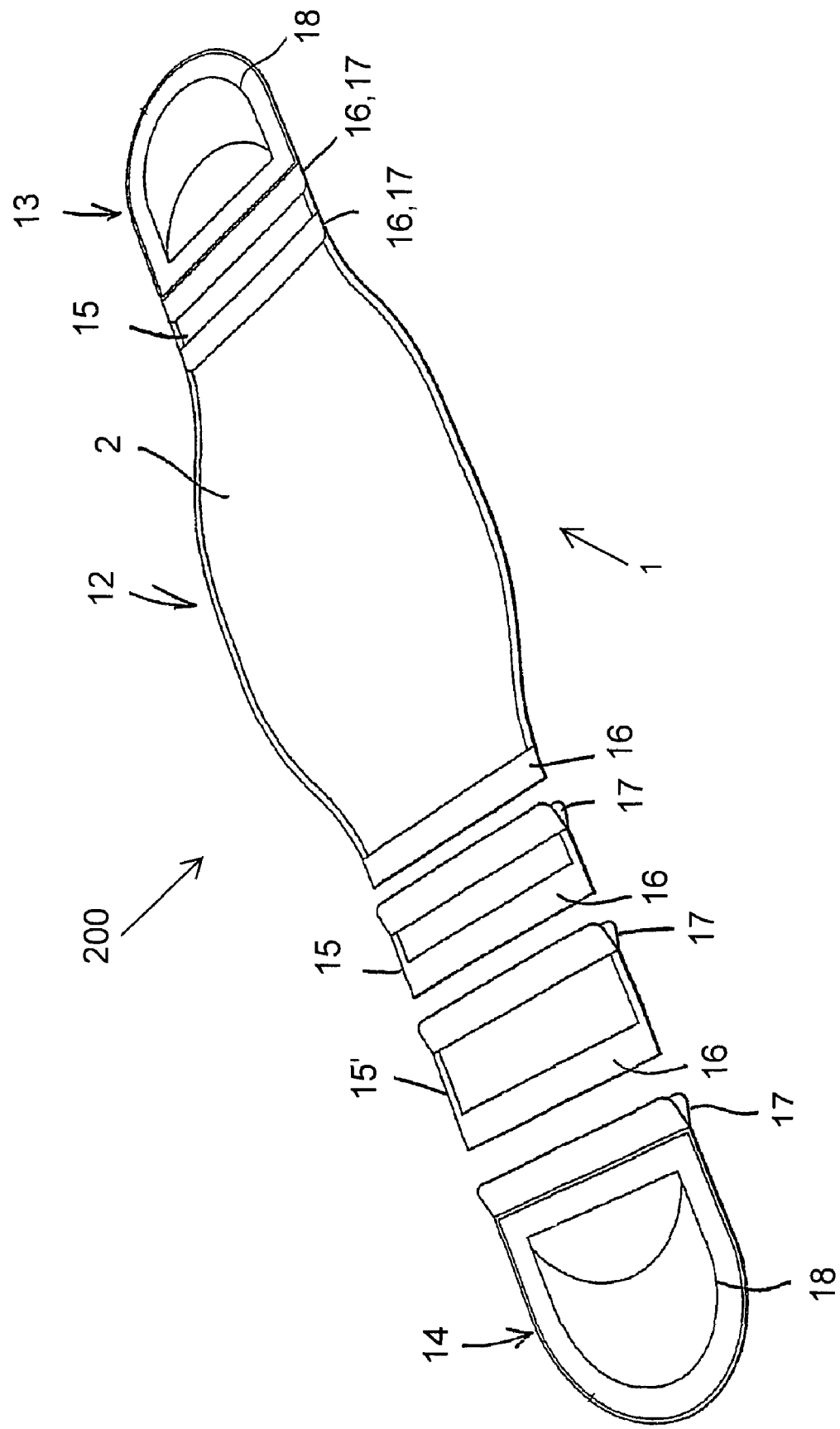
FIG. 1 shows a perspective view of a multipart bandage (not joined together) laid out flat.
Figure 2:
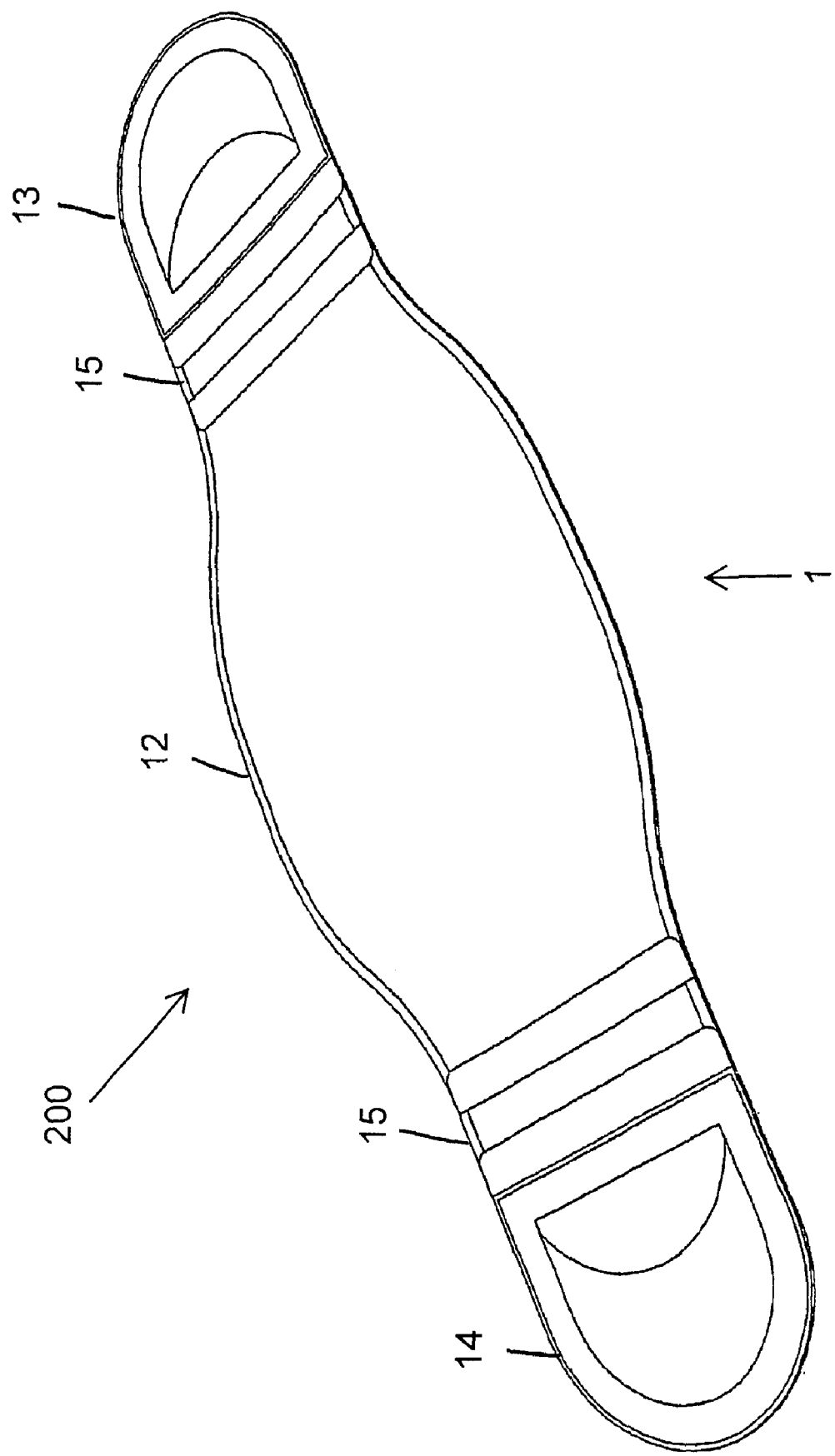
FIG. 2 shows a perspective view as in FIG. 1 of a bandage joined together for a desired length.

FIGS. 1-3 show a lower back orthosis 200, in which the bandage 1 is formed of several pieces, including a middle piece 12 forming the wider middle area 2 and end pieces 13 and 14. The central piece 12 provides an increased surface area of contact on the lower back of the patient. The end pieces 13, 14, which have narrower width that the wider area of the middle piece, are releasably securable to one another around the patient's abdomen. Between the middle piece 12 and the end pieces 13, 14 it is possible to insert intermediates pieces 15, 15'.

Intermediate pieces 15, 15' can be inserted between the middle piece 12 and the end pieces 13, 14 to adjust the length of the orthosis 200. Intermediate pieces 15, 15' may have different lengths so that bandages of different lengths can be created. In FIG. 1, an inserted intermediate piece 15 is releasably secured between the middle piece 12 and the end piece 13. On the left side proximate the end piece 14, intermediate pieces 15 and 15' which may be releasably secured to the bandage 1, are shown separated from the middle piece 2 and the end piece 14 at locations where they can be inserted into the bandage 1. When the intermediate pieces 15, 15' of the right length to suit the abdominal girth of a patient have been selected, they are securely connected to the associated end piece 13, 14 and the middle piece 2.

The connection between the middle piece 12, end pieces 13, 14 and/or intermediate pieces 15, is achieved by the use of attachment elements and counter attachment elements. As illustrated in FIG. 1, the intermediate pieces 15, 15' each have a flat end 16 which faces the end pieces 13, 14, and attachment elements disposed on either side of the flat ends. The end pieces 13, 14 have mouth-like ends 17 which face the intermediate pieces 15, 15' and which are releasably securable over both sides of the flat ends 16 of the intermediate pieces 15, 15' by a counter attachment element. An example of a suitable attachment and counter attachment element includes, but is not limited to, Velcro® fasteners. In a corresponding manner, the middle piece 12 has flat ends 16 with attachment elements which releasably secure to the counter attachment elements of mouth-like ends 17 of either the end pieces 13, 14 or the intermediate pieces 15, 15'. FIG. 1 shows further that, on their outer surfaces (the upper faces in the drawing), the end pieces 13, 14 have a pocket 18 into which the patient can insert his hands to secure the bandage 1 around his lower back with a certain amount of traction.

FIG. 2 shows the assembled, ready-to-use bandage 1 after selection and insertion of the appropriate intermediate pieces 15, 15'. If the patient's girth is small, the bandage 1 can also be assembled without an intermediate pieces 15, 15' by securing the end pieces 13, 14 directly to the middle piece 12.

FIG. 3 shows the bandage 1 with a support device 5' and a tightening strap 8'. The support device 5' includes ribs 26, which are arranged next to one another and connected to one another at their central areas by connectors such as tongues or spring elements 27, which may be formed in one piece with the ribs 26.

The invention claimed is:

1. A bandage configured to extend around a body part of a patient, the bandage comprising:
    a middle piece having a length defined by first and second ends;
    a first end piece that is adapted to form a releasably securable connection to the first end of the middle piece;
    a second end piece that is adapted to form a releasably securable connection to the second end of the middle piece;
    at least a first intermediate piece that is adapted to form a releasably securable connection between one of the first end piece and the first end of the middle piece and the second end piece and the second end of the middle piece, the first intermediate piece having a flat portion including two outer surfaces each bearing fastener elements and a bifurcated portion having two inner surfaces each bearing fastener counter-elements.

2. The bandage of claim 1, further comprising a support element attached to the middle piece.

3. The bandage of claim 2, wherein the support element comprises a plurality of ribs connected to each other by a plurality of spring elements.

4. The bandage of claim 1, wherein the first intermediate piece is releasably securable by inserting the flat portion of the first intermediate piece into a corresponding bifurcated portion of the first end piece and inserting a flat portion of the first end of the middle piece into the bifurcated portion of the first intermediate piece.

5. The bandage of claim 1, further comprising a second intermediate piece that is releasably securable between the second end piece and the second end of the middle piece, the first intermediate piece having a flat portion including two outer surfaces each bearing fastener elements and a bifurcated portion having two inner surfaces each bearing fastener counter-elements.

6. The bandage of claim 5, wherein
    the second intermediate piece is releasably securable by inserting the flat portion of the second intermediate piece into a corresponding bifurcated portion of the second end piece and inserting a flat portion of the middle piece into the bifurcated portion of the second intermediate piece.

7. The bandage of claim 5, further comprising a third intermediate piece that is releasably securable between the first end piece and the first intermediate piece.

8. The bandage of claim 7, wherein the first intermediate portion, the second intermediate portion and the third intermediate portion have different lengths.

9. The bandage of claim 1, wherein the fastener elements and the fastener counter-elements comprise, in combination, hook-and-loop fasteners.

10. A method of positioning a bandage around a patient's lower back and abdomen, the bandage including a middle piece having first and second ends and a widened portion for supporting the lower back, and two end pieces which are releasably securable at one end to the middle piece and at the other end to one another, the method comprising:
    determining the patient's girth around the lower back and abdomen;
    optionally forming a releasably securable connection between the first end of the middle piece and an adjacent end of a first intermediate piece based on the patient's girth;
    optionally forming a releasably securable connection between the second end of the middle piece and an adjacent end of a second intermediate piece based on the patient's girth;
    forming a releasably securable connection between the first end piece and one of the first end of the middle piece and an adjacent end of the first intermediate piece;
    forming a releasably securable connection between the second end piece and one of the second end of the middle piece and an adjacent end of the second intermediate piece,
    wherein each of the first and second intermediate pieces include an end having a flat portion with two outer surfaces each bearing fastener elements and an end having a bifurcated portion with two inner surfaces each bearing fastener counter-elements;

positioning the bandage around the patient; and releasably securing the first and second end piece to one another adjacent the patient's abdomen.

11. The method of claim 10, further comprising optionally forming a releasably securable connection between at least a third intermediate piece between the first end piece and the middle piece to increase the length of the lower back orthosis.

12. The method of claim 10, further comprising attaching a support element to the middle piece.

13. A bandage adapted to extend around a lower back and abdomen of a patient, the bandage comprising:

a middle piece having a length defined by first and second ends and a widened area disposed between the first and second ends;

first and second end pieces which are releasably securable to the respective first and second ends of the middle piece, and which are releasably securable to one another, wherein the width of the widened area is greater than a width of the first and second end pieces;

a first intermediate piece which is releasably securable to the first end of the middle piece and to the first end piece; and a second intermediate piece which is releasably securable to the second end of the middle piece and to the second end piece; and a support element attached to the middle piece, the support element comprising a plurality of ribs connected to each other by a plurality of spring elements;

wherein the first and second intermediate pieces are optionally releasably secured between the middle piece and respective end pieces to increase the length of the bandage.

* * * * *